(12) United States Patent
Andrews et al.

(10) Patent No.: US 7,303,708 B2
(45) Date of Patent: Dec. 4, 2007

(54) SUPER ABSORBENT DISTRIBUTION SYSTEM DESIGN FOR HOMOGENEOUS DISTRIBUTION THROUGHOUT AN ABSORBENT CORE

(75) Inventors: Robert E. Andrews, Sheboygan, WI (US); Chris J. Nelson, Plymouth, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 217 days.

(21) Appl. No.: 11/102,908

(22) Filed: Apr. 8, 2005

(65) Prior Publication Data

US 2005/0234412 A1    Oct. 20, 2005

Related U.S. Application Data

(60) Provisional application No. 60/563,517, filed on Apr. 19, 2004.

(51) Int. Cl.
*A61F 13/15* (2006.01)

(52) U.S. Cl. .................. 264/121; 264/122; 264/518; 425/80.1; 425/83.1

(58) Field of Classification Search .................. None
See application file for complete search history.

(56) References Cited

U.S. PATENT DOCUMENTS

| 135,145 | A | 1/1873 | Murphy |
| 293,353 | A | 2/1884 | Purvis |
| 312,257 | A | 2/1885 | Cotton et al. |
| 410,123 | A | 8/1889 | Stilwell |
| 432,742 | A | 7/1890 | Stanley |
| 643,821 | A | 2/1900 | Howlett |
| 1,393,524 | A | 10/1921 | Grupe |
| 1,605,842 | A | 11/1926 | Jones |
| 1,957,651 | A | 5/1934 | Joa |
| 2,009,857 | A | 7/1935 | Potdevin |
| 2,054,832 | A | 9/1936 | Potdevin |
| 2,128,746 | A | 8/1938 | Joa |

(Continued)

FOREIGN PATENT DOCUMENTS

CA    1146129    5/1983

(Continued)

OTHER PUBLICATIONS

Reciprocating Mechanisms, Ingenious Mechanisms for Designers and Inventors, Franklin Jones vol. 1.

*Primary Examiner*—Mary Lynn Theisen
(74) *Attorney, Agent, or Firm*—Ryan, Kromholz and Manion, S.C.

(57) ABSTRACT

A super absorbent distribution system for homogenous distribution throughout an absorbent core is disclosed. A super absorbent material is injected into a stream of absorbent fluff at an opposite direction to that of the stream of absorbent fluff. The super absorbent is blasted into the peak and outer surface of a cone shaped super absorbent barrier. The oncoming absorbent fluff also contends with a similarly shaped absorbent fluff barrier. The super absorbent material slows down as it hits the super absorbent barrier and oncoming fluff, then stops, then reverses direction and flows with the absorbent fluff as a homogenous distribution of super absorbent material and absorbent fluff. The combination of super absorbent material and absorbent fluff may encounter baffle members to further distribute the super absorbent material and absorbent fluff.

8 Claims, 9 Drawing Sheets

U.S. PATENT DOCUMENTS

| | | |
|---|---|---|
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 7/1958 | Joa |
| 2,842,169 A | 7/1958 | Joa |
| 2,851,934 A | 9/1958 | Heywood |
| 2,875,724 A | 3/1959 | Joa |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,772,120 A | 11/1973 | Radzins |
| 3,796,360 A | 3/1974 | Alexeff |
| 3,816,210 A | 6/1974 | Aoko et al. |
| 3,854,917 A | 12/1974 | McKinney et al. |
| 3,883,389 A | 5/1975 | Schott, Jr. |
| 3,888,400 A | 6/1975 | Wiig |
| 3,904,147 A | 9/1975 | Taitel et al. |
| 3,918,698 A | 11/1975 | Coast |
| 3,960,646 A | 6/1976 | Wiedamann |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,094,319 A | 6/1978 | Joa |
| 4,106,974 A | 8/1978 | Hirsch |
| 4,108,584 A | 8/1978 | Radzins et al. |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,215,827 A | 8/1980 | Roberts et al. |
| 4,222,533 A | 9/1980 | Pongracz |
| 4,223,822 A | 9/1980 | Clitheroe |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,342,206 A | 8/1982 | Rommel |
| 4,364,787 A | 12/1982 | Radzins |
| 4,374,576 A | 2/1983 | Ryan |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisnecki et al. |
| 4,701,239 A | 10/1987 | Craig |
| 4,726,874 A | 2/1988 | VanVliet |
| 4,726,876 A | 2/1988 | Tomsovic et al. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,795,510 A | 1/1989 | Wittrock et al. |
| 4,801,345 A | 1/1989 | Dussaud et al. |
| 4,802,570 A | 2/1989 | Hirsch et al. |
| 4,840,609 A | 6/1989 | Jones et al. |
| 4,880,102 A | 11/1989 | Indrebo |
| 4,888,231 A | 12/1989 | Angstadt |

| Patent | Date | Inventor |
|---|---|---|
| 4,892,536 A | 1/1990 | Des Marais et al. |
| 4,904,440 A | 2/1990 | Angstadt |
| 4,908,175 A | 3/1990 | Angstadt |
| 4,925,520 A | 5/1990 | Beaudoin et al. |
| 4,927,322 A | 5/1990 | Schweizer et al. |
| 4,927,582 A * | 5/1990 | Bryson ................. 264/113 |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A | 9/1991 | Bay |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,195,684 A | 3/1993 | Radzins |
| 5,213,645 A | 5/1993 | Nomura et al. |
| 5,223,069 A | 6/1993 | Tokuno et al. |
| 5,226,992 A | 7/1993 | Morman |
| 5,246,433 A | 9/1993 | Hasse et al. |
| 5,267,933 A | 12/1993 | Precoma |
| 5,308,345 A | 5/1994 | Herrin |
| 5,340,424 A | 8/1994 | Matsushita |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,429,788 A * | 7/1995 | Ribble et al. ................. 264/510 |
| 5,435,802 A | 7/1995 | Kober |
| 5,447,677 A * | 9/1995 | Griffoul et al. ............. 264/510 |
| 5,449,353 A | 9/1995 | Watanabe et al. |
| 5,464,401 A | 11/1995 | Hasse et al. |
| 5,494,622 A | 2/1996 | Heath et al. |
| 5,540,647 A | 7/1996 | Weiermann et al. |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 5,602,747 A | 2/1997 | Rajala |
| 5,624,420 A | 4/1997 | Bridges et al. |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| RE35,687 E | 12/1997 | Igaue et al. |
| 5,693,165 A | 12/1997 | Schmitz |
| 5,707,470 A | 1/1998 | Rajala et al. |
| 5,711,832 A | 1/1998 | Glaug et al. |
| 5,745,922 A | 5/1998 | Rajala et al. |
| 5,746,869 A | 5/1998 | Hayden et al. |
| 5,749,989 A | 5/1998 | Linman et al. |
| 5,788,797 A | 8/1998 | Herrin et al. |
| 5,817,199 A | 10/1998 | Brennecke et al. |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,879,500 A | 3/1999 | Herrin et al. |
| 5,932,039 A | 8/1999 | Popp et al. |
| 5,964,970 A | 10/1999 | Woolwine et al. |
| 6,036,805 A | 3/2000 | McNichols |
| 6,050,517 A | 4/2000 | Dobrescu et al. |
| 6,074,110 A | 6/2000 | Verlinden et al. |
| 6,098,249 A | 8/2000 | Toney et al. |
| 6,123,792 A | 9/2000 | Samida et al. |
| 6,183,576 B1 | 2/2001 | Couillard et al. |
| 6,210,386 B1 | 4/2001 | Inoue |
| 6,264,784 B1 | 7/2001 | Menard et al. |
| 6,267,575 B1 * | 7/2001 | Rooyakkers et al. ....... 425/83.1 |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,336,921 B1 | 1/2002 | Kato et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,473,669 B2 | 10/2002 | Rajala et al. |
| 6,475,325 B1 | 11/2002 | Parrish et al. |
| 6,478,786 B1 | 11/2002 | Gloug et al. |
| 6,482,278 B1 | 11/2002 | McCabe et al. |
| 6,494,244 B2 | 12/2002 | Parrish et al. |
| 6,521,320 B2 | 2/2003 | McCabe et al. |
| 6,524,423 B1 | 2/2003 | Hilt et al. |
| 6,533,989 B1 * | 3/2003 | Wisneski et al. ............ 264/510 |
| 6,551,228 B1 | 4/2003 | Richards |
| 6,551,430 B1 | 4/2003 | Glaug et al. |
| 6,554,815 B1 | 4/2003 | Umebayashi |
| 6,572,520 B2 | 6/2003 | Blumle |
| 6,596,108 B2 | 7/2003 | McCabe |
| 6,605,172 B1 | 8/2003 | Anderson et al. |
| 6,605,173 B2 | 8/2003 | Glaug et al. |
| 6,648,122 B1 | 11/2003 | Hirsch et al. |
| 6,649,010 B2 | 11/2003 | Parrish et al. |
| 6,659,991 B2 | 12/2003 | Suckane |
| D497,991 S | 11/2004 | Otsubo et al. |
| 6,820,671 B2 | 11/2004 | Calvert |
| 6,837,840 B2 | 1/2005 | Yonekawa et al. |
| 6,840,616 B2 | 1/2005 | Summers |
| 6,875,202 B2 | 4/2005 | Kumasaka et al. |
| 7,077,393 B2 | 7/2006 | Ishida |
| 7,214,174 B2 | 5/2007 | Allen et al. |
| 2001/0012813 A1 | 8/2001 | Bluemie |
| 2001/0017181 A1 | 8/2001 | Otruba et al. |
| 2001/0042948 A1 * | 11/2001 | Sorensen .................... 264/518 |
| 2002/0046802 A1 | 4/2002 | Tachibana et al. |
| 2002/0059013 A1 | 5/2002 | Rajala et al. |
| 2003/0000620 A1 | 1/2003 | Herrin et al. |
| 2003/0052148 A1 | 3/2003 | Rajala et al. |
| 2003/0066585 A1 | 4/2003 | McCabe |
| 2003/0083638 A1 | 5/2003 | Malee |
| 2003/0084984 A1 | 5/2003 | Glaug et al. |
| 2003/0089447 A1 | 5/2003 | Molee et al. |
| 2003/0135189 A1 | 7/2003 | Umebayashi |
| 2004/0016500 A1 | 1/2004 | Tachibana et al. |
| 2005/0000628 A1 | 1/2005 | Norrley |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |

| | | | | | |
|---|---|---|---|---|---|
| 2006/0224137 | A1 | 10/2006 | McCabe et al. | | |
| 2006/0265867 | A1 | 11/2006 | Schaap | | |
| 2007/0074953 | A1 | 4/2007 | McCabe | | |

FOREIGN PATENT DOCUMENTS

| | | | | | |
|---|---|---|---|---|---|
| CA | 1153345 | 9/1983 | EP | 0652175 | 5/1995 |
| CA | 1190078 | 7/1985 | EP | 0901780 | 3/1999 |
| CA | 1210744 | 9/1986 | EP | 1132325 | 9/2001 |
| CA | 1212132 | 9/1986 | EP | 1272347 | 1/2003 |
| CA | 1236056 | 5/1988 | EP | 1707168 | 4/2006 |
| CA | 1249102 | 1/1989 | ES | 509706 | 11/1982 |
| CA | 1292201 | 11/1991 | ES | 520559 | 12/1983 |
| CA | 1307244 | 9/1992 | ES | 296211 | 12/1987 |
| CA | 1308015 | 9/1992 | FR | 2891811 | 4/2007 |
| CA | 1310342 | 11/1992 | GB | 191101501 | 1/1912 |
| CA | 2023816 | 3/1994 | GB | 439897 | 12/1935 |
| CA | 2404154 | 10/2001 | JP | 428364 | 1/1992 |
| CA | 2541194 | 1/2006 | JP | 542180 | 2/1993 |
| CA | 2559517 | 5/2007 | JP | 576566 | 3/1993 |
| DE | 102006047280 | 4/2007 | JP | 626160 | 2/1994 |
| EP | 0048011 | 3/1982 | JP | 626161 | 2/1994 |
| EP | 0089106 | 9/1983 | JP | 6197925 | 7/1994 |
| EP | 0304140 | 8/1987 | JP | 10-277091 | 10/1998 |
| EP | 0439897 | 2/1990 | SE | 0602047 | 5/2007 |
| EP | 0455231 | 11/1991 | WO | WO9907319 | 2/1999 |
| EP | 510251 | 10/1992 | WO | WO9913813 | 3/1999 |
| | | | WO | WO9965437 | 12/1999 |
| | | | WO | WO0143682 | 6/2001 |
| | | | WO | WO0172237 | 10/2001 |
| | | | WO | WO2005075163 | 1/2005 |

* cited by examiner

SUPER ABSORBENT DISTRIBUTION SYSTEM DESIGN FOR HOMOGENEOUS DISTRIBUTION THROUGHOUT AN ABSORBENT CORE

RELATED APPLICATION

This application claims the benefit of U.S. Provisional Patent Application Ser. No. 60/563,517, filed 19 Apr. 2004, and entitled "Super Absorbent Distribution System Design for Homogeneous Distribution Throughout an Absorbent Core."

BACKGROUND OF THE INVENTION

This invention relates to a method and apparatus for forming an absorbent core having a multiplicity of components. More particularly, the present invention relates to a method and apparatus for producing a homogeneous distribution of super absorbent material throughout an absorbent core.

Absorbent articles including bandages, disposable diapers, and sanitary napkins, generally include an absorbent core that has a multiplicity of components so as to improve the article's absorption and retention characteristics. These absorbent cores have had their total absorbency improved greatly by the addition of super absorbent material to the commonly used absorbent fibrous materials.

Typically, the absorbent fibrous material is composed of cellulose wadding or cellulosic wood pulp material commonly referred to as "fluff", although a mixture of natural and synthetic fibers is within the scope of the invention. An absorbent core composed of wood pulp fluff is typically formed by employing conventional air laying techniques.

The ability of these absorbent cores to manage the typical surges of liquid flow is heavily dependent on the proper distribution of super absorbent material within the absorbent fluff. When most super absorbent materials absorb aqueous fluids, they swell substantially, often to double their dry dimensions or more at saturation. As these super absorbent materials absorb fluid and swell, they generally become a gelatinous mass. If the super absorbent material is in a particulate form and the particles are close to one another, they can create a phenomenon known as "gel-blocking," wherein the saturated blocks of super absorbent material inappropriately provide a barrier to additional surges of liquid.

Thus, for maximum effectiveness of the super absorbent material, absorbent structures which include such materials in particulate form preferably maintain separation of the particles from one another to permit maximum absorption and swelling without allowing the particles to coalesce and form the gel barrier.

To avoid this barrier and to optimize performance, various modes of distribution of super absorbent material throughout the absorbent core have been tried. Layering and blending the super absorbent material within the absorbent core make up the principle two modes. Examples of generally layered applications can be seen in U.S. Pat. No. 4,551,191 issued Nov. 5, 1985 to Kock et al. and U.S. Pat. No. 6,416,697 issued Jul. 9, 2002 to Venturino et al. In this method, super absorbent material is commonly distributed onto a moving porous web. Examples of blended applications can be seen in U.S. Pat. No. 4,764,325 issued Aug. 16, 1988 to Angstadt and U.S. Pat. No. 4,927,582 issued May 22, 1990 to Bryson. In a blended application, the super absorbent material first is mixed with the absorbent fluff. Then the mixture is laid down creating the absorbent structure.

Super absorbent material typically has the consistency of sand, while absorbent fluff is more fibrous, and tends to knit together. High concentrations of super absorbent material, if not distributed amongst the fluff fibers, performs poorly and tends to fall out of the product during manufacturing—a loss of investment.

Manufacturers have attempted to optimize distribution of the super absorbent material in order to get the most "bang for the buck" out of their investment. As well, optimizing the distribution and eliminating localized buildup of super absorbent material can improve the feel of the article on the user. For example, eliminating a localized buildup of super absorbent material along an inner layer of a diaper can eliminate the gritty feel of the super absorbent material next to the baby's skin, making for a much happier baby and a more effective diaper.

Likewise, there has been a trend in reducing the bulk of diapers, in attempts to make them more like underwear and to take up less shelf space in retailer's outlets. Generally, the thinner the diaper, the higher the concentration of super absorbent material required to produce the same level of absorbency. High levels of super absorbent material, however, tend to be more difficult to control and to maintain in position.

In solving these problems, the most friendly application of super absorbent material would seem to be a completely uniform (homogeneous) distribution, with no noticeable local concentrations of super absorbent material. To achieve homogenous blending, it is necessary to add the super absorbent material to the main air stream that carries the absorbent fluff to the deposition molds that form the cores.

Super absorbent material, however, has entirely different behavior from fluff fibers. It has a much higher density (thus a higher inertia) and does not easily follow the fluff fibers along their turbulent paths to their final, intended resting place. Once it has been imparted with a velocity, the super absorbent material tends to behave more like a bullet than a leaf in the wind. This all makes it difficult to mix the super absorbent material uniformly with the absorbent fluff. It is a problem of uniformly blending two very different components.

The prior art super absorbent distribution techniques such as those herein described earlier have made attempts in providing substantially uniform distribution of the particulate super absorbent material. However, none of the foregoing appears to have adequately understood and addressed the problems associated with the entirely different behaviors of the super absorbent material and the fluff fibers.

Because of the foregoing deficiencies in the art, an object of the present invention is to provide a method and apparatus that solves these problems by making the distribution of the super absorbent material within the fluff fibers more uniform. Homogeneous distribution can be achieved by essentially altering the behavior of the super absorbent material to make its behavior more closely replicate that of the absorbent fluff in which it must uniformly mix.

SUMMARY OF THE INVENTION

The present invention comprises a unique method and apparatus for injecting super absorbent material into a main fluff-carrying air stream. Specifically, the present invention provides a novel super absorbent distribution system for homogenous distribution of the super absorbent material throughout the absorbent fluff. The super absorbent materials to be used with the present invention may be manufactured from a variety of materials. A wide variety of super absorbent materials are known to those skilled in the art. See, for example, U.S. Pat. No. 4,076,663 issued Feb. 28, 1978 to Masuda et al, U.S. Pat. No. 4,286,082 issued Aug. 25, 1981 to Tsubakimoto et al., U.S. Pat. No. 4,062,817 issued Dec. 13, 1977 to Westerman, and U.S. Pat. No. 4,340,706 issued Jul. 20, 1982 to Obayashi et al. Additionally, the super absorbent materials to be used with the present invention may be of varying common dimensions.

The invention uses a unique method and apparatus for injecting super absorbent material into the main fluff-carrying air stream. The invention directs the super absorbent material upstream into the oncoming path of the absorbent fluff, but first impinges the stream of super absorbent material against the peak of a cone-shaped barrier, which flares the stream of super absorbent material particles outward, causing them to slow down and to reverse their direction, joining the absorbent fluff stream at a point and at a velocity which carries the super absorbent material along, as though they were part of the same stream of fluff fibers. The cone-shaped barrier also distributes the super absorbent material with relative uniformity, thereby enhancing the objective of achieving homogenous distribution.

In addition to the reverse flow insertion of the stream of super absorbent material, an additional component in the operation of this invention includes the addition of "speed bumps," which may be baffle members inserted to disrupt the continuity of the air stream, further distributing the super absorbent material and absorbent fluff throughout the fiber lay-down process.

Again, an objective of this invention is to inject the stream of super absorbent material particles into the stream of air-entrained fluff fibers so that they may most naturally assume the velocity and trajectory of the fluff fibers. The effect is achieved as the particles of super absorbent material are distributed with relative uniformity throughout the absorbent pad.

It is another object of the present invention to provide an apparatus for and method of making airlaid absorbent cores having discrete particles of super absorbent material homogenously dispersed throughout the absorbent core.

It is a further object of the present invention to provide an apparatus for and method of making absorbent cores having a multiplicity of components.

It is also an object of the present invention to provide an apparatus for and method of making an absorbent core having a multiplicity of components, at least one of the components containing a particular amount of discrete particles of a super absorbent material.

DESCRIPTION OF THE PREFERRED EMBODIMENT

Figure 1:
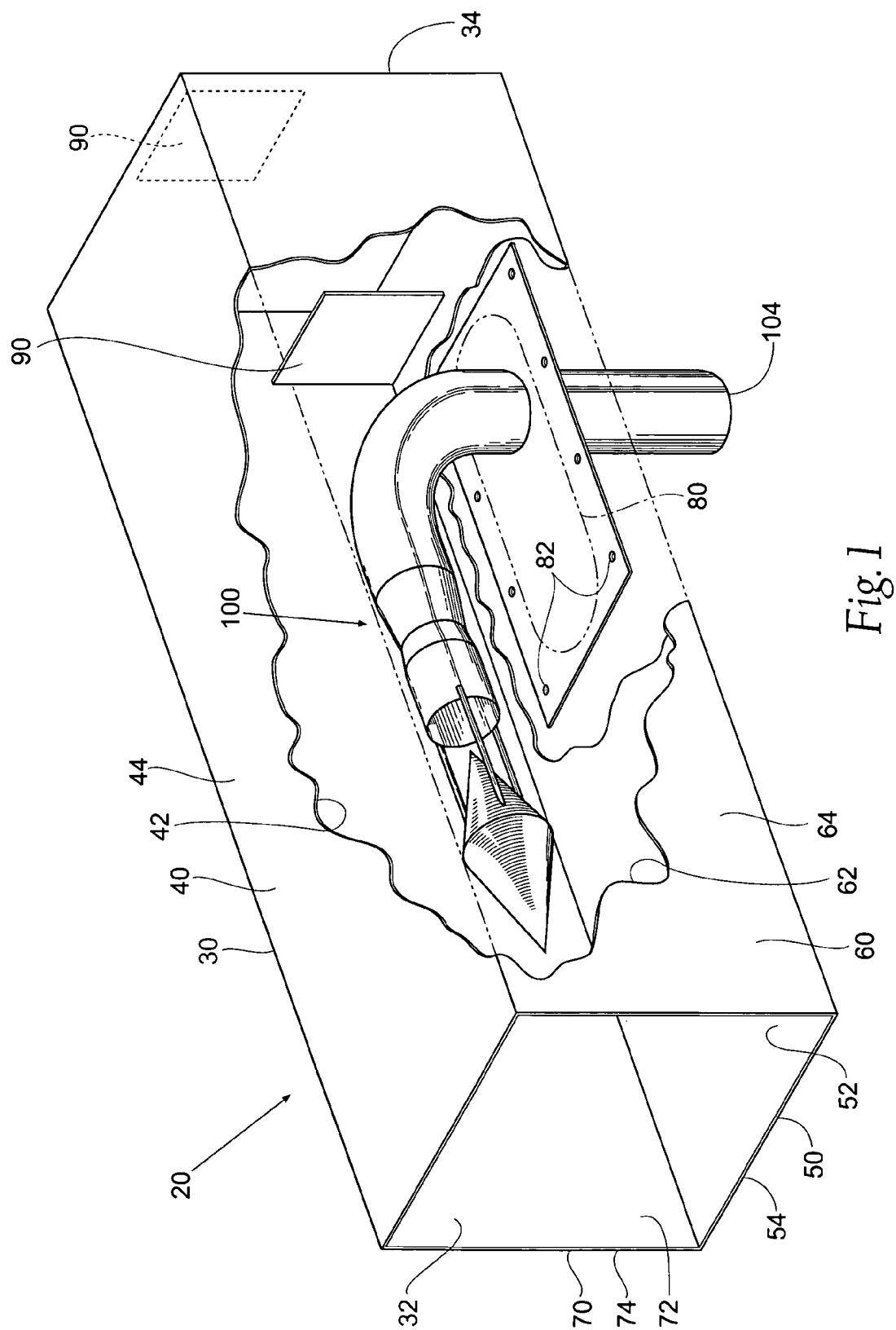
FIG. 1 is a perspective view of a distribution system that embodies the present invention.

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention.

Referring to the drawings, wherein like numerals represent like parts throughout the views, there is generally designated at 20 a distribution system according to the present invention. As seen particularly in FIGS. 1 and 2, the distribution system 20 includes a diffuser housing 30 and a diffuser conduit assembly 100 for homogenous mixing of super absorbent material 22 and absorbent fluff 26.

The diffuser housing 30 preferably comprises a top wall 40, a bottom wall 50, a first side wall 60, and a second side wall 70. The top wall 40 includes an inside surface 42 and an outside surface 44. The bottom wall 50 also includes an inside surface 52 and an outside surface 54. The first side wall 60 includes an inside surface 62 and an outside surface 64. The second side wall 70 also includes an inside surface 72 and an outside surface 74. The diffuser housing 30 also may include an inlet end 32 and an outlet end 34.

Figure 2:
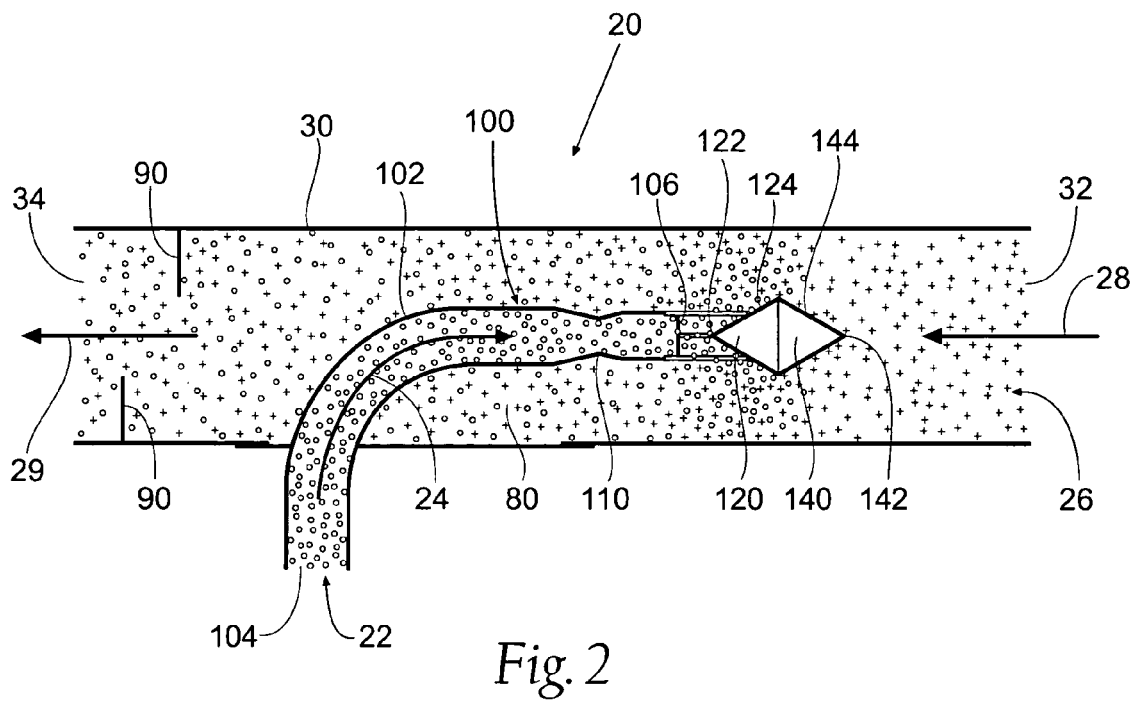
FIG. 2 is a side elevation view of the distribution system shown in FIG. 1, showing the injection of super absorbent material into the absorbent fluff air stream, and the resulting homogenous distribution of super absorbent material and absorbent fluff.

As further illustrated in the view of FIGS. 1 and 2, the distribution system 20 includes a diffuser conduit assembly 100 coupled to the diffuser housing 30. Disposed within any of the top wall 40, bottom wall 50, first side wall 60, or second side wall 70 is a diffuser conduit assembly aperture 80. Diffuser housing mounting hole apertures 82 preferably are positioned around the diffuser conduit assembly aperture 80 in order to couple the aforementioned diffuser conduit assembly 100 to the diffuser housing 30, by way of bolt and nut fasteners (not shown), although it is within the scope of the invention to couple the diffuser conduit assembly 100 to the diffuser housing 30 by other conventional means such as welding or riveting.

As best seen in FIG. 1, the diffuser conduit assembly 100 preferably is coupled to the diffuser housing 30 and may be partially disposed within the diffuser housing 30. In a preferred embodiment, the diffuser conduit inlet end 104 partially extends outside the diffuser housing 30 when the diffuser conduit assembly 100 is attached to the diffuser housing 30.

Figure 3:
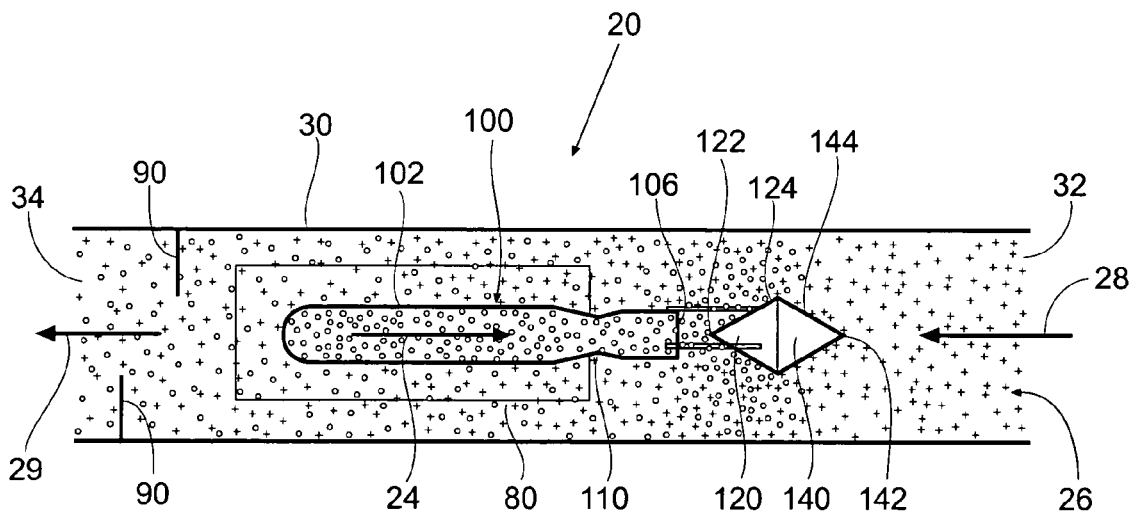
FIG. 3 is a top plan view of the distribution system shown in FIG. 2.
Figure 4A:
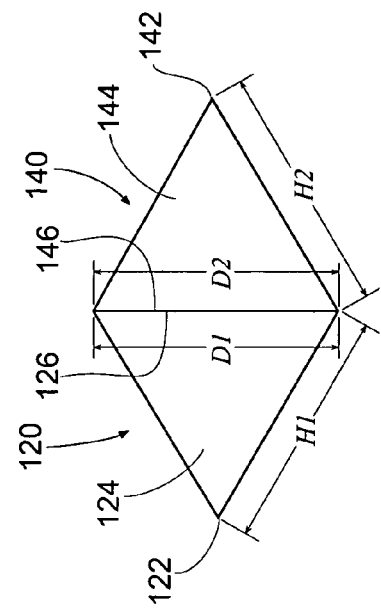
FIG. 4a is a front view of a preferred embodiment of a fluff barrier.
Figure 6:
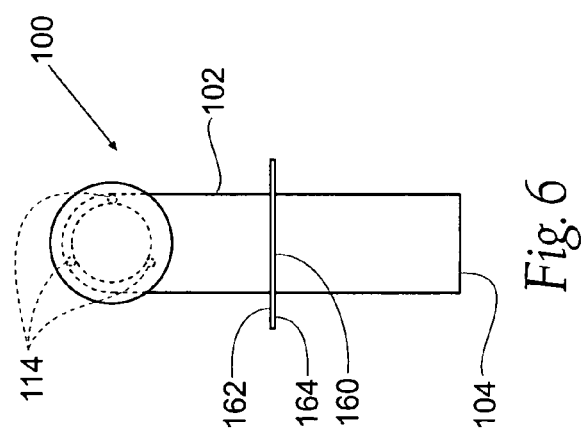
FIG. 6 is a front elevation view of the diffuser conduit assembly shown in FIG. 4.
Figure 4:
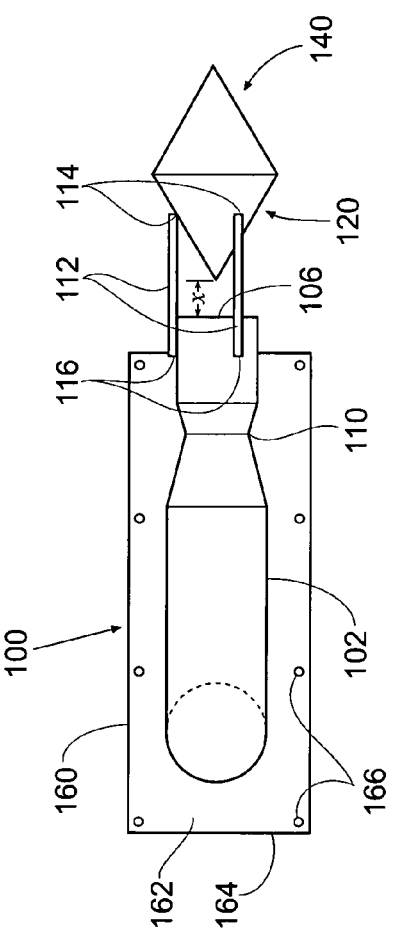
FIG. 4 is a top plan view of the diffuser conduit assembly of the distribution system shown in FIG. 1.
Figure 5:
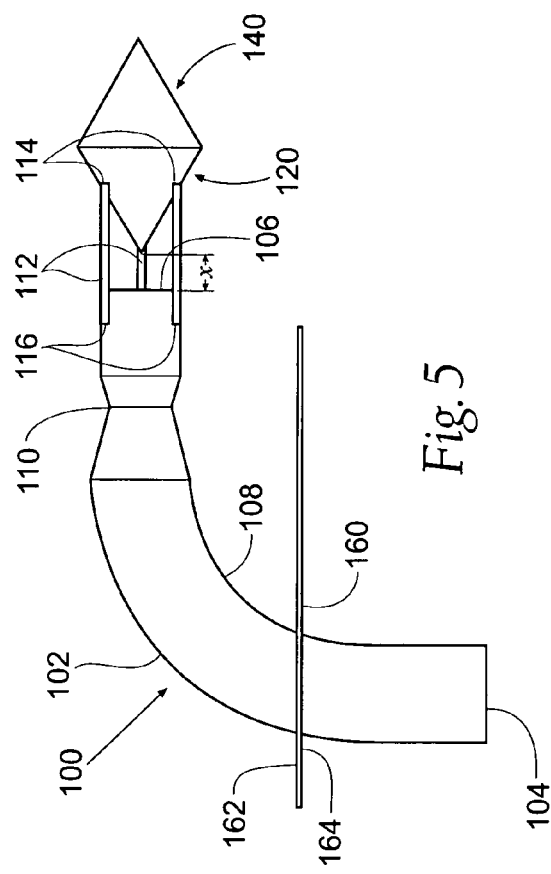
FIG. 5 is a side elevation view of the diffuser conduit assembly shown in FIG. 4.

Now referring to FIGS. 4, 5, and 6, the diffuser conduit assembly 100 preferably comprises a diffuser conduit 102 with an inlet end 104 and an outlet end 106. The diffuser conduit 102 may also include an arc shaped bend 108 and a venturi 110 (shown best in FIG. 5), the venturi 110 being preferably located nearer the outlet end 106 than the inlet end 104. The diffuser conduit venturi 110 accelerates the super absorbent material 22 before it is injected into the oncoming flow path 28 of the absorbent fluff 26 (shown in FIGS. 2 and 3).

Coupled to the outlet end 106 of the diffuser conduit 102 are preferably three support rods 112, although more or less support rods 112 may be used and remains within the scope of the invention. The support rods 112 have a first end 114 and a second end 116, wherein the second end 116 is coupled to the diffuser conduit 102.

As best seen in FIGS. 4, 4a, and 5, coupled to the first end 114 of the support rods 112 is preferably a cone shaped super absorbent barrier 120. Facing toward the outlet end 106 of the diffuser conduit 102, the cone shaped barrier 120 includes a peak 122 and an outer surface 124. The outer surface 124 includes a predetermined outer surface height H1. The cone shaped super absorbent barrier 120 also includes a base 126, having a base diameter D1, positioned at an opposite end to that of the peak 122. The peak 122 of the cone shaped super absorbent barrier 120 is preferably positioned at a predetermined distance X away from the outlet end 106 of the diffuser conduit 102.

The cone shaped super absorbent barrier 120 has coupled to its base 126 a similarly shaped cone shaped fluff barrier 140. In the preferred embodiment, the cone shaped fluff barrier 140 is a mirror image of the cone shaped super absorbent barrier 120. The cone shaped fluff barrier 140 also includes a peak 142 and an outer surface 144. The outer surface 144 includes a predetermined outer surface height H2. The cone shaped fluff barrier 140 also includes a base 146, having a base diameter D2, positioned at an opposite end to that of the peak 142. The peak 142 of the cone shaped fluff barrier 140 faces away from the outlet end 106 of the diffuser conduit 102.

Referring now to FIG. 4, also included with the diffuser conduit assembly 100 may be a mounting plate 160. The mounting plate 160 has a first side 162 and a second side 164. A plurality of apertures 166 are disposed within the mounting plate 160 in order to secure the mounting plate 160 to the diffuser housing 30 using a nut and bolt configuration (not shown) or other conventional means.

Referring now to FIG. 6, a front elevation view of the diffuser conduit assembly 100 is shown, correlating to FIG. 4.

Figure 7:
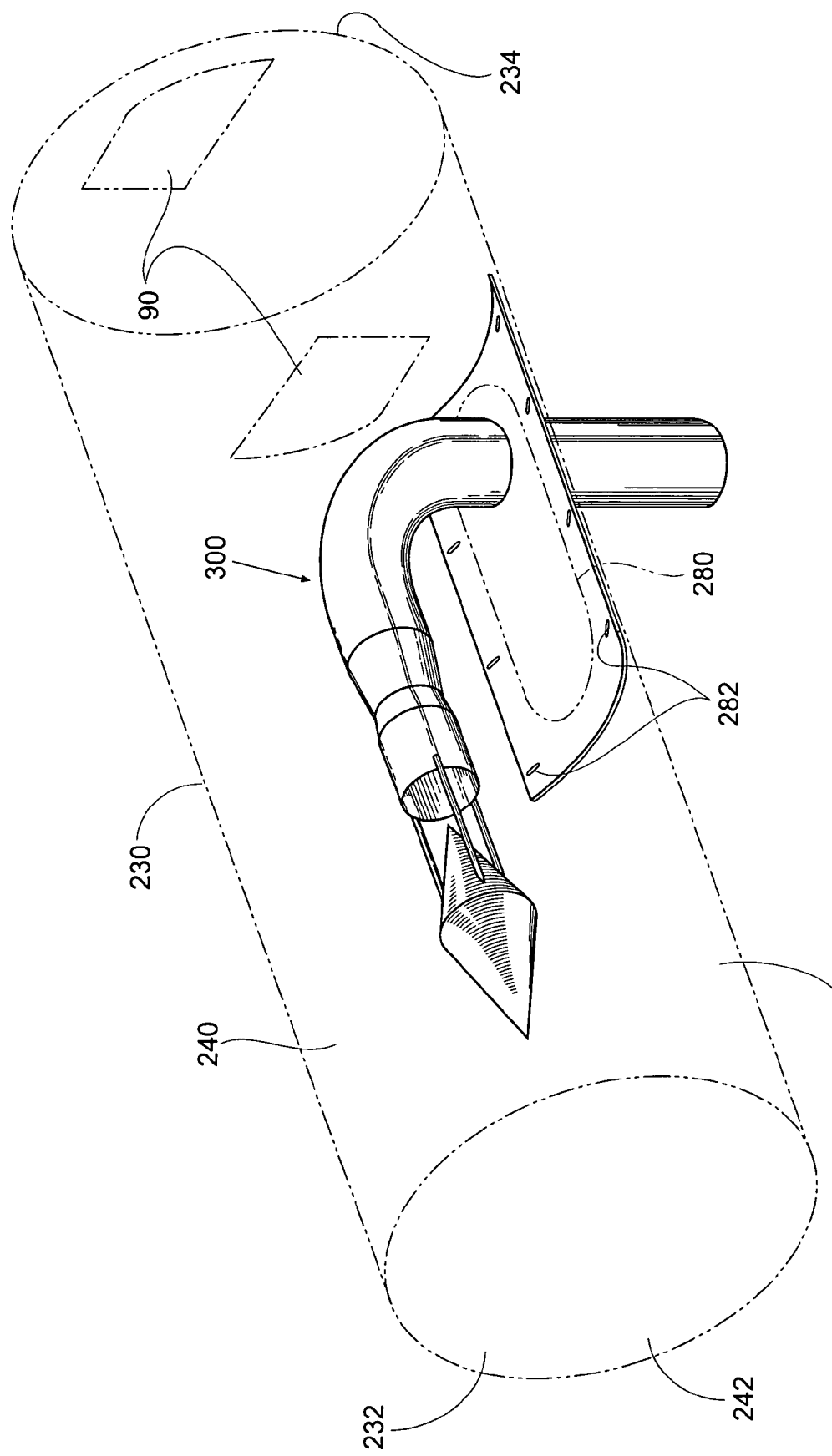
FIG. 7 is a perspective view of an alternative embodiment of the distribution system shown in FIG. 1, wherein the diffuser housing is tubular in shape.

As viewed in FIG. 7, in an additional alternative embodiment, the distribution system disclosed may include a tubularly shaped diffuser housing 230. The tubular diffuser housing 230 preferably includes an inlet end 232 and an outlet end 234. The tubular housing 230 circumferential wall 240 comprises an inside surface 242 and an outside surface 244. Disposed within the circumferential wall 240 may be a diffuser conduit assembly aperture 280 and a plurality of diffuser housing mounting hole apertures 282. Baffle members 90 may also be employed in this embodiment.

Figure 8:
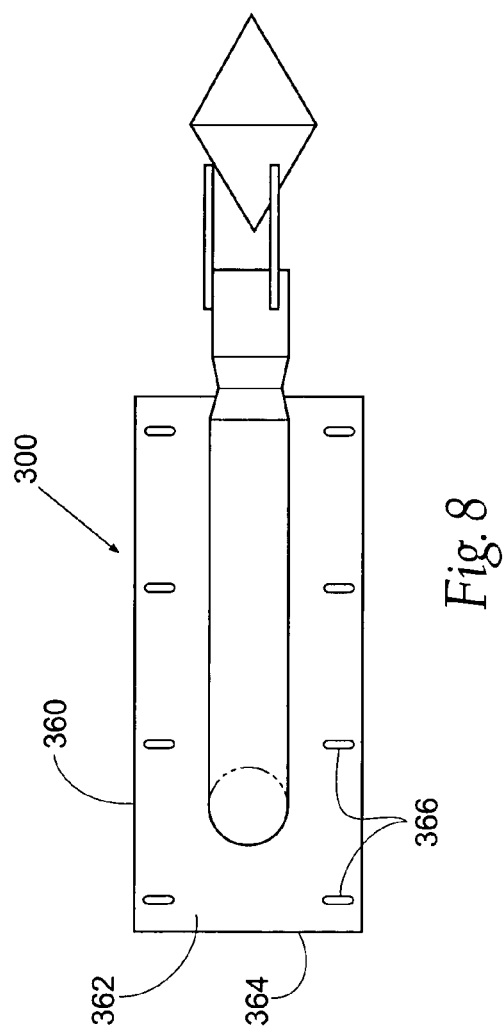
FIG. 8 is a top plan view of the diffuser conduit assembly for the alternative embodiment of the distribution system shown in FIG. 7, wherein the mounting plate is arced.
Figure 10:
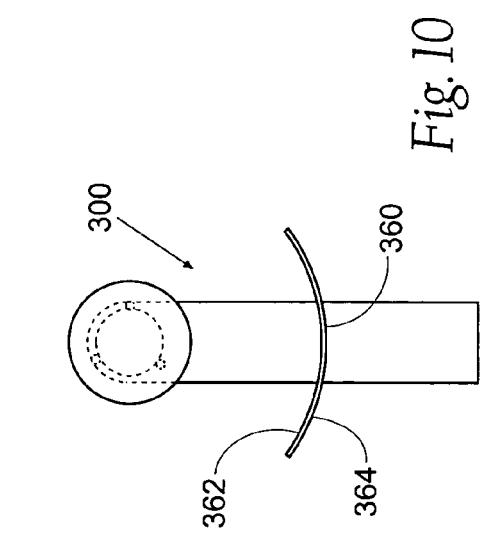
FIG. 10 is a front elevation view of the diffuser conduit assembly for the alternative embodiment of the distribution system shown in FIG. 7, wherein the mounting plate is arced.
Figure 9:
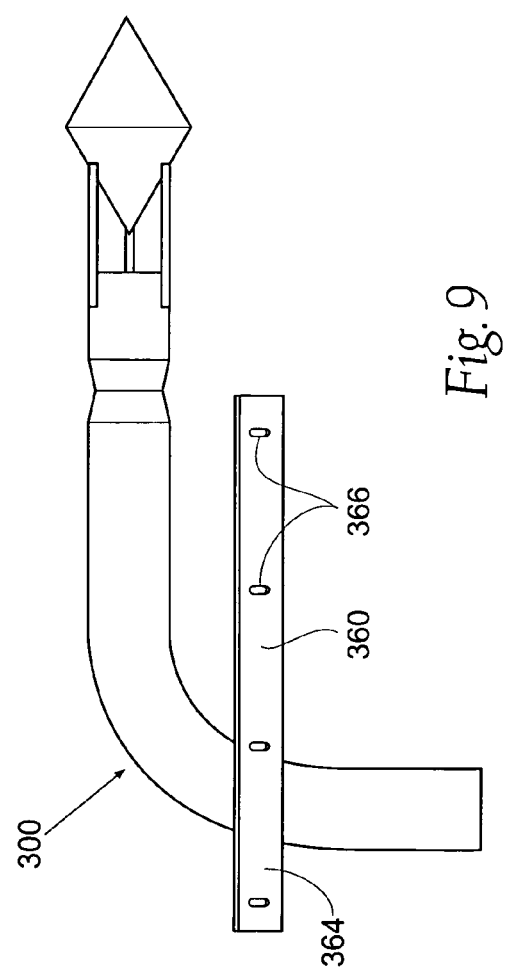
FIG. 9 is a side elevation view of the diffuser conduit assembly for the alternative embodiment of the distribution system shown in FIG. 7, wherein the mounting plate is arced.

As best seen in FIGS. 8, 9 and 10, included with the diffuser conduit assembly 300 is an arced mounting plate 360 if the alternative tubuluarly shaped diffuser housing 230 is employed. The arced mounting plate 360 includes a first side 362 and a second side 364. Disposed within the arced mounting plate 360 is a plurality of mounting plate apertures 366. The mounting plate apertures 366 are provided to receive a nut and bolt combination (not shown) or other commonly known in the art fastening mechanisms.

Figure 11:
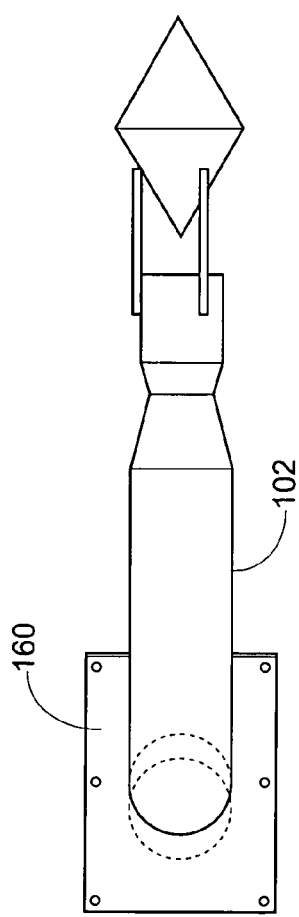
FIG. 11 is a top plan view of an alternative embodiment of a diffuser conduit assembly, wherein the diffuser conduit extends through the mounting plate at a predetermined angle.
Figure 12:
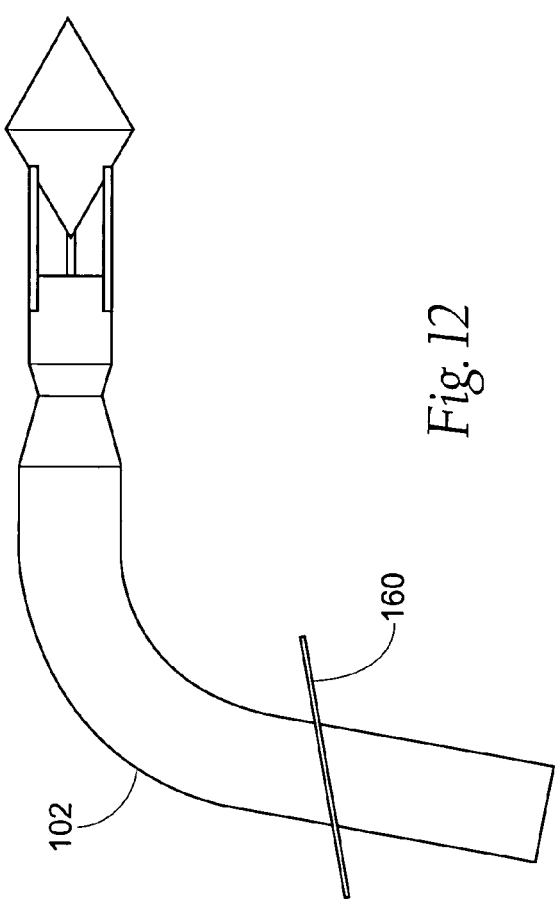
FIG. 12 is a side elevation view of the alternative embodiment of the diffuser conduit assembly shown in FIG. 11, wherein the diffuser conduit extends through the mounting plate at a predetermined angle.
Figure 13:
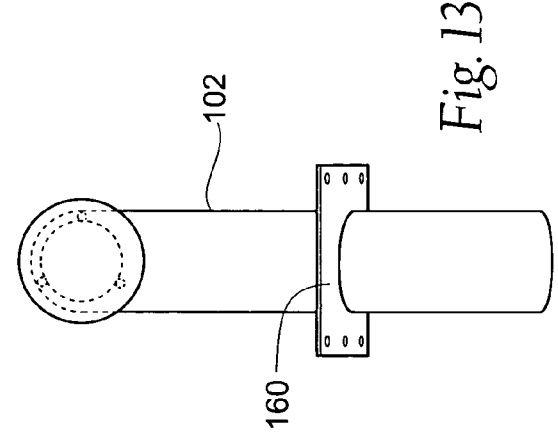
FIG. 13 is a front elevation view of the alternative embodiment of the diffuser conduit assembly shown in FIG. 11, wherein the diffuser conduit extends through the mounting plate at a predetermined angle.

As viewed in FIGS. 11, 12, and 13, in another embodiment, the diffuser conduit 102 may extend through the mounting plate 160 at a predetermined angle.

Figure 14:
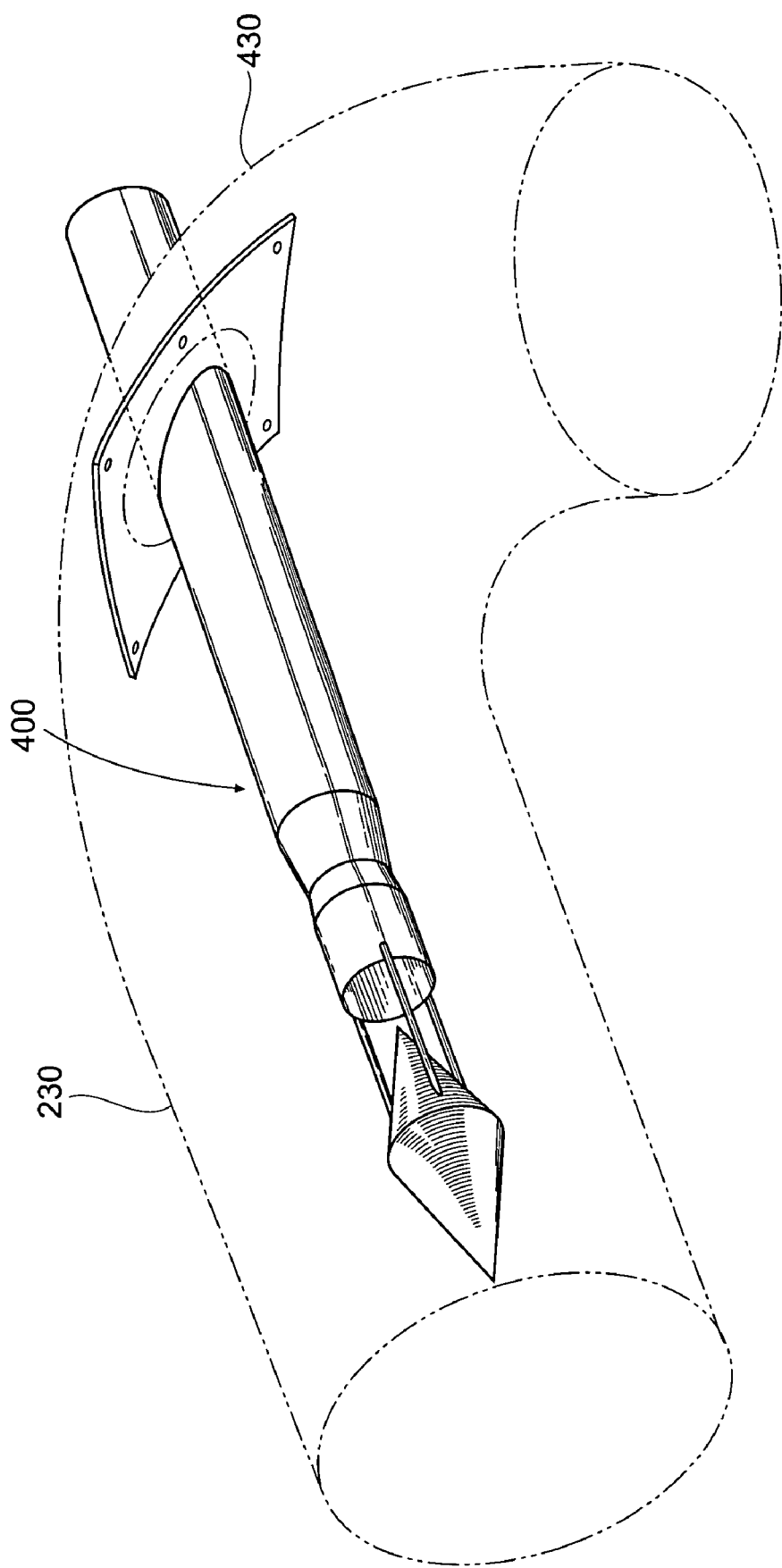
FIG. 14 is a perspective view of an alternative embodiment of a diffuser conduit assembly, wherein the diffuser conduit assembly is essentially linear and enters the diffuser housing at a curved portion of the diffuser housing.

As seen particularly in FIG. 14, in still yet another embodiment, the diffuser conduit assembly 400 may be essentially linear and enter the diffuser housing 230 at a curved portion of the diffuser housing 430.

Figure 15:
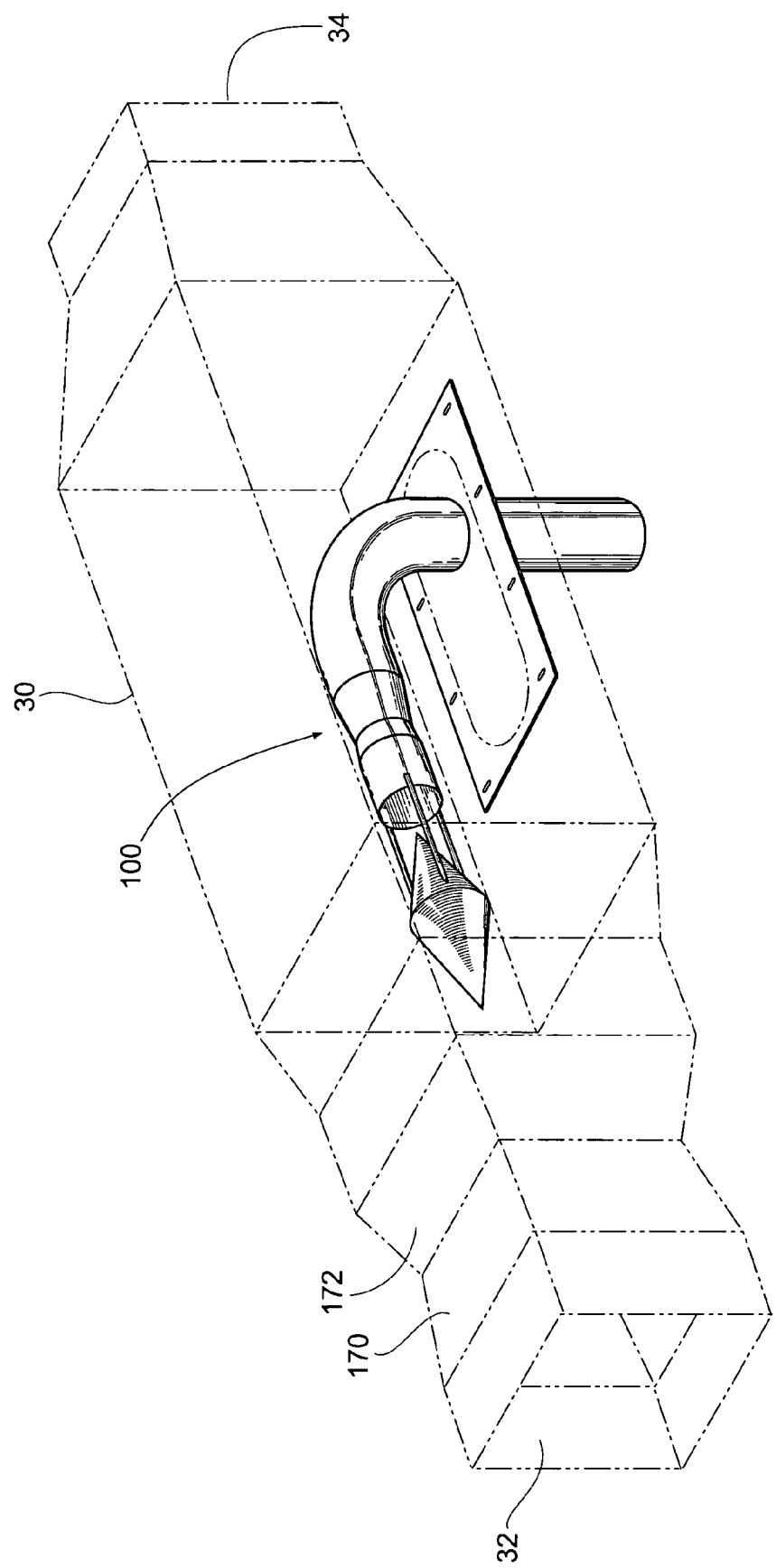
FIG. 15 is a perspective view of an alternative embodiment of the distribution system of FIG. 1, wherein the diffuser housing includes an increase in cross sectional flow area and a decrease in cross sectional flow area.

Referring to FIG. 15, in an alternative embodiment, the diffuser housing 30 may also include at least one increase in cross sectional flow area 170 as measured in a direction substantially perpendicular to the direction of flow, between the diffuser housing 30 inlet end 32 and outlet end 34. As well, the diffuser housing 30 may also include at least one decrease in cross sectional flow area 172, again as measured in a direction substantially perpendicular to the direction of flow, between the diffuser housing 30 inlet end 32 and outlet end 34.

Figure 16:
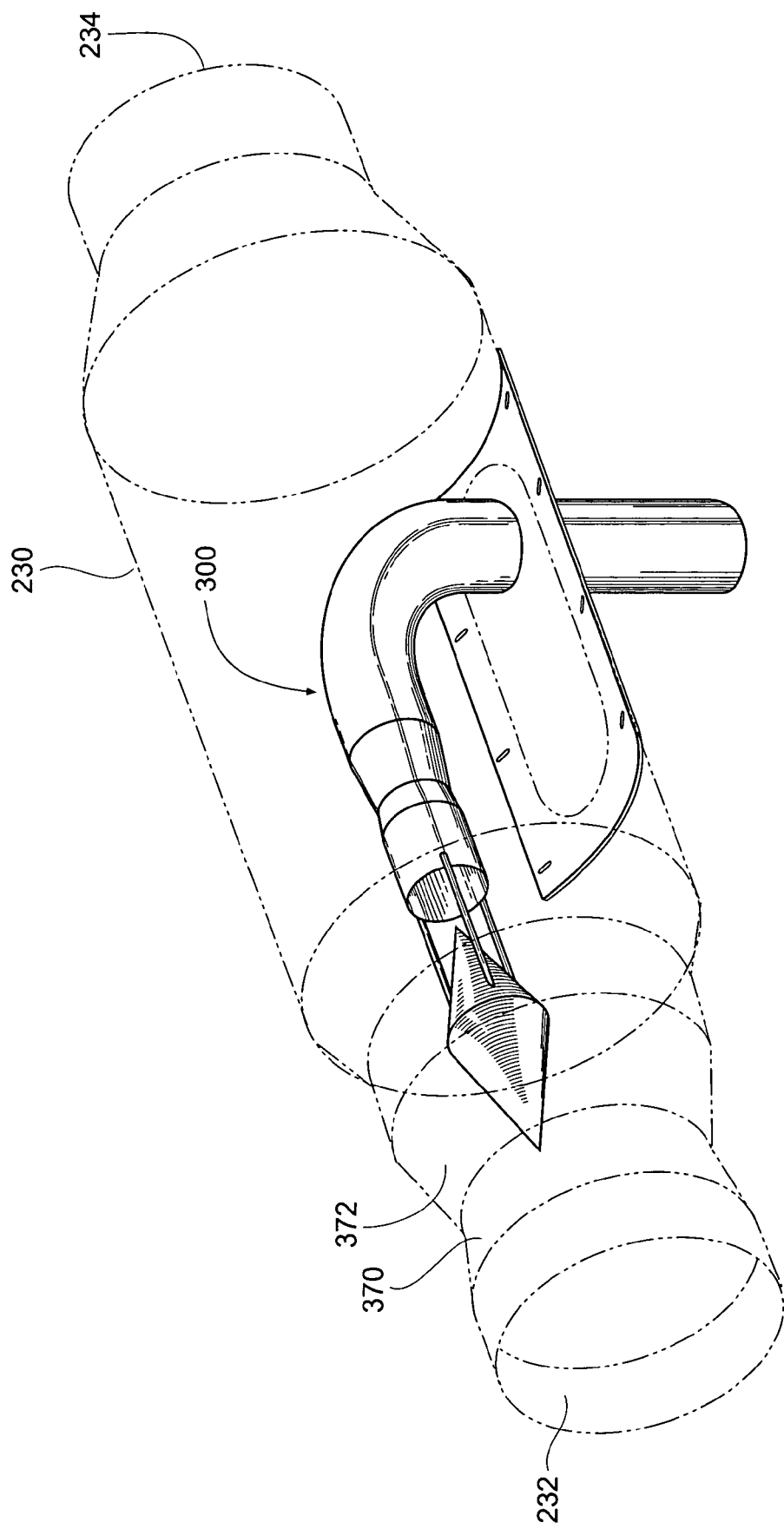
FIG. 16 is a perspective view of an alternative embodiment of the distribution system of FIG. 7, wherein the diffuser housing includes an increase in cross sectional flow area and a decrease in cross sectional flow area.

Referring now to FIG. 16, in yet another embodiment, the tubular diffuser housing 230 may also include at least one increase in cross sectional flow area 370 as measured in a direction substantially perpendicular to the direction of flow, between the diffuser housing 230 inlet end 232 and outlet end 234. As well, the diffuser housing 230 may also include at least one decrease in cross sectional flow area 372, again as measured in a direction substantially perpendicular to the direction of flow, between the diffuser housing 230 inlet end 232 and outlet end 234.

Method of Operation

With the structure of the distribution system 20 described, a description of the operation of the distribution system 20 will now be provided.

In order to simplify the disclosure, several elements or means that can readily be supplied by those skilled in the art have been omitted from the Figures. Such elements may include super absorbent material supply means, fluff generator and supply means, vacuum supply means, absorbent core forming means, absorbent core takeaway means, controlling means, and the like. It should be readily appreciated, however, that the present invention can be configured and employed to produce absorbent structures in conjunction with a variety of different machinery components, and the absorbent structures can be incorporated into various types of absorbent articles, such as diapers, feminine care products, incontinence garments, bandages, absorbent pads and the like.

As best seen in FIGS. 2 and 3, a predetermined amount of super absorbent material 22 with a predetermined velocity (dependent on the size of the material) and entrained in an air stream is supplied to the inlet end 104 of the diffuser conduit 102 by any delivery means commonly known in the art. Preferably at the same time, a predetermined amount of absorbent fluff 26, also with a predetermined velocity and entrained in an air stream, is supplied to the inlet end 32 of the diffuser housing 30 by any delivery means commonly known in the art. The super absorbent material 22 takes on a flow path 24 while the absorbent fluff 26 also takes on a flow path 28.

As the super absorbent material 22 streams through the diffuser conduit 102, its velocity is increased when it passes through the diffuser venturi 110. The super absorbent material 22 is then blasted out the diffuser conduit 102 outlet end 106 and into the peak 122 and outer surface 124 of the cone shaped super absorbent barrier 120.

At the same time, the stream of absorbent fluff 26 is blasted through the diffuser housing 30 and into the peak 142 and outer surface 144 of the cone shaped fluff material barrier 140. Because the super absorbent material 22 is blasted into the super absorbent barrier 120 and fluff flow path 28 in an opposite direction to that of the fluff flow path 28, the super absorbent material 22 slows down, then it stops, changes direction, and now flows with the absorbent fluff 26, taking on a combined flow path 29 of super absorbent material 22 and absorbent fluff 26. The invention does not blow the super absorbent material 22 into the same direction as the fluff flow path 28 as is done in many prior art devices.

As the combination of super absorbent material 22 and absorbent fluff 26 stream through the diffuser housing 30, they preferably encounter baffle members 90 which disrupt the air stream and the combined flow path 29, further distributing the super absorbent material 22 and fluff 26 in order to create the homogenous distribution.

With further regard to baffle members, in FIGS. 1 and 7, in still yet another embodiment, baffle members 90 may be secured to a wall 40, 50, 60, 70, 230, of the diffuser housing 30 or 230.

With further reference to FIGS. 15 and 16, in an alternative embodiment, the diffuser housings 30 and 230 may include at least one increase in cross sectional flow area 170 and 370, and may also include at least one decrease in cross sectional flow area 172 and 372. These increases and decreases in flow area act as venturis to alter the velocity of the absorbent fluff 26 as it enters the diffuser housings 30 and 230, and to alter the combined super absorbent material 22 and absorbent fluff 26 as it exits the diffuser housings 30 and 230, allowing for a more uniform distribution. The increases and decreases in flow area also act to disrupt the flow stream, again improving the distribution of super absorbent material 22 and fluff 26.

As further illustrated in the views of FIGS. 1, 2, and 3, absorbent fluff 26 enters the diffuser housing 30 inlet end 32, super absorbent material enters the diffuser conduit 102 inlet end 104, and a homogenous mixture of super absorbent material 22 and fluff 26 exit the diffuser housing 30 at the outlet end 34. To achieve the objective of homogenous blending, it is necessary to inject the super absorbent material 22 into the oncoming air stream path 28 that carries the fluff 26. The homogenous mixture is then entrained in the combined air stream 29 to the deposition molds commonly used in the art that form the absorbent cores.

The method for homogenous distribution according to this invention preferably comprises the steps of:

a. delivering a stream of super absorbent material 22 and air into the inlet end 104 of a diffuser conduit 102 in order to create a super absorbent stream;

b. delivering a stream of absorbent fluff 26 and air into the inlet end 32 of a diffuser housing 30 in order to create an absorbent fluff stream;

c. entraining the super absorbent 22 stream in the air;

d. entraining the absorbent fluff 26 stream in the air; and e. directing the super absorbent 22 stream toward a cone shaped super absorbent barrier 120 and directing the absorbent fluff 26 stream toward a cone shaped fluff barrier 140 so as to inject the super absorbent material 22 into the absorbent fluff 26 stream at an opposite direction to that of the absorbent fluff 26 stream, thereby creating a homogenous stream of super absorbent material 22 and fluff 26.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:

1. A method of producing a homogeneous distribution of super absorbent material, the method comprising:
    introducing an absorbent material into an air stream, said air stream and said first material traveling in a first direction;
    introducing a super absorbent material into said air stream, said second material introduced in a direction opposite said first direction.

2. A method of producing a homogeneous distribution of super absorbent material, the method comprising:
    introducing a stream of super absorbent material into an inlet end of a diffuser conduit;
    introducing a stream of absorbent fluff into an inlet end of a diffuser housing;
    directing the super absorbent stream toward a first barrier and directing the absorbent fluff stream toward a second barrier so as to inject the super absorbent material into the absorbent fluff stream at an opposite direction to that of the absorbent fluff stream.

3. A distribution system for homogenous distribution of super absorbent material, the distribution system comprising:
    a housing carrying a stream of absorbent fluff in a first direction;
    a conduit carrying a stream of super absorbent material in a second direction said second direction being generally opposite said first direction, said conduit coupled with said housing,
    said conduit discharging said super absorbent material into said housing, said super absorbent material decelerating in said housing, and changing direction from said second direction to said first direction.

4. A system according to claim 3, said system further comprising a plurality of baffle members for disrupting the flow of an air stream within said housing for distributing the super absorbent material within the absorbent fluff.

5. A system according to claim 3, said conduit comprising a diffuser conduit having an inlet end and an outlet end, the diffuser conduit having an arc bend.

6. A system according to claim 5, said system further comprising a venturi in said diffuser conduit.

7. A system according to claim 3, said system further comprising a fluff barrier coupled to said housing to deflect said stream of absorbent fluff from entering said stream of super absorbent material in said second direction.

8. A system according to claim 7, said fluff barrier conically shaped.

* * * * *